United States Patent [19]

Periana et al.

[11] Patent Number: 5,068,407
[45] Date of Patent: Nov. 26, 1991

[54] OXIDATION OF TERTIARY-ALKYL SUBSTITUTED AROMATICS

[75] Inventors: Roy A. Periana, San Jose, Calif.; George F. Schaefer, Olivette, Mo.

[73] Assignee: Monsanto Company, St. Louis, Mo.

[21] Appl. No.: 473,031

[22] Filed: Jan. 31, 1990

[51] Int. Cl.$^5$ .......................................... C07C 41/265
[52] U.S. Cl. .............................. 562/416; 502/224; 562/417; 562/480
[58] Field of Search ............................ 562/416, 417

[56] References Cited

U.S. PATENT DOCUMENTS

| | | | |
|---|---|---|---|
| 2,833,816 | 5/1958 | Saffer et al. | 562/416 |
| 2,833,817 | 5/1958 | Saffer et al. | 562/416 |
| 2,833,818 | 5/1958 | Landau et al. | 562/416 |
| 2,833,819 | 5/1958 | Egbert et al. | 562/416 |
| 2,833,820 | 5/1958 | Egbert et al. | 562/416 |
| 3,089,907 | 5/1963 | Saffer et al. | 562/416 |
| 3,296,280 | 1/1967 | Peterson | 562/410 X |
| 3,383,402 | 5/1968 | Yunick | 560/77 |
| 3,631,097 | 12/1971 | Christmann et al. | 562/410 |
| 3,636,082 | 1/1972 | Knowles | 560/76 |

FOREIGN PATENT DOCUMENTS

| | | |
|---|---|---|
| 0206543 | 12/1986 | European Pat. Off. |
| 267774 | 11/1987 | European Pat. Off. |
| 57-149243 | 9/1982 | Japan |
| 2155921 | 10/1985 | United Kingdom |

OTHER PUBLICATIONS

Sheldon and Kochi, "Metal-Catalyzed Oxidations of Organic Compounds", Academic Press, p. 316, (1981).
H. D. Holtz, *J. Org. Chem.*, vol. 37, No. 13, pp. 2069–2074, (1972).

*Primary Examiner*—Jose G. Dees
*Assistant Examiner*—Vera C. Clarke
*Attorney, Agent, or Firm*—Banner, Birch McKie & Beckett

[57] ABSTRACT

A process for the production of para-oriented dicarboxylic aromatic acids is disclosed in which an aromatic compound, having a tertiary alkyl group, is oxidized with molecular oxygen in the presence of a catalytic composition comprising a cobalt salt, a minor amount of a manganese salt, and a source of chloride in the presence of a solvent.

9 Claims, No Drawings

OXIDATION OF TERTIARY-ALKYL SUBSTITUTED AROMATICS

FIELD OF THE INVENTION

This invention relates to the production of aromatic acids by catalytic oxidation of aromatic compounds with alkyl substituents, using molecular oxygen, and to a novel, halogen-containing catalyst for the oxidation of tertiary-alkyl substituted aromatic compounds.

BACKGROUND OF THE INVENTION

Di-tertiary-alkylation of aromatic compounds produces almost exclusively the p,p'-isomer due to stereoelectronic effects of the bulky tertiary-alkyl (t-alkyl) group. However, aromatic compounds with t-alkyl substituents are difficult to oxidize to the acids. As reported in Sheldon and Kochi, *Metal-Catalyzed Oxidations of Organic Compounds*, "Alkyl aromatic compounds without benzylic C-H bonds (e.g., t-butylbenzene) are, of course, unreactive toward auto-oxidation." Examples in U.S. Pat. Nos. 2,833,816 and 3,089,907, which disclose the oxidation of alkyl aromatics, clearly show that t-butyl groups are resistant to oxidation.

Auto-oxidation of alkyl aromatics to produce aromatic acids was disclosed in a series of five patents issued in 1958, Saffer et al., U.S. Pat. Nos. 2,833,816-20. These patents taught the use of heavy metal carboxylate salts as catalysts, in particular, manganese carboxylates. In U.S. Pat. No. 2,833,816, the disclosed catalyst contains a heavy metal or mixture of metals (manganese, cobalt, nickel, chromium, vanadium, molybdenum, tungsten, tin or cerium, preferably manganese or cobalt), an aliphatic acid of 1-8 carbons, and a source of bromine to serve as a promoter. The metal can be provided as the metal, as a metal complex or as a salt, with the preferred form being as the salt of an aliphatic carboxylic acid. Mixed metal catalysts are exemplified by a mixture containing one part cobalt and one-to-three parts manganese. The bromine promoter can be supplied as elemental bromine, hydrobromic acid, an ionic bromide salt, or an organic bromine-containing compound. The metal bromide salt, which may be added directly or formed during the reaction from the above sources of these components, should be present at 0.1-10% by weight, based on the concentration of the aromatic reactant. The aromatic compounds which may be oxidized in the presence of this catalyst contain alkyl groups attached through either primary or secondary alkyl carbons. U.S. Pat. No. 3,089,907, a continuation-in-part of the application that became U.S. Pat. No. 2,833,816, shows that t-butyl groups attached to an aromatic ring are not oxidized in this system, even when methyl groups attached to the same ring are being oxidized to carboxyl groups. A specific example is given of oxidation of t-butyl-m-xylene to t-butyl-isophthalic acid.

Holz, in *J. Org. Chem.*, volume 37, pages 2069-74 (1972), studied the oxidation of alkyl-substituted benzene and reported that t-butyltoluene could be oxidized by molecular oxygen to terephthalic acid by using cobalt chloride as catalyst instead of cobalt bromide; however, the yield of terephthalic acid was very low. The catalyst used in this study was cobalt acetate with hydrochloric acid in a mixed solvent of acetic acid and chlorobenzene.

Para,para'-dicarboxypolyphenyls (p,p'-dicarboxypolyphenyls) are of great interest to the art of high performance liquid crystal polymers. For example, replacing terephthalic acid with 4,4'-dicarboxybiphenyl or 4,4'-dicarboxy-p-terphenyl imparts greater rigidity and stability to polyester polymers, with resulting improvement in performance characteristics. However, up to now such benefits have been unavailable in the art, because an environmentally safe, economical method for the preparation of the p,p'-dicarboxypolyphenyls was lacking.

A number of methods for preparation of 4,4'-dicarboxybiphenyl have been described in the prior art, although none of them have found commercial application. UK Patent 2,155,921 teaches carboxylation of 4-alkylbiphenyl in the presence of $HF/BF_3$ followed by oxidation of the alkyl group. This process has the disadvantage of requiring stoichiometric amounts of an expensive component, HF. Another expensive route is taught in Japanese Patent Application JP 57/149,243, now issued as JP 83/46,494. In this patent, 4,4'-dicarboxybiphenyl is formed from the dipotassium salt of diphenic acid which can be isomerized with Cd catalysts at high temperature in the presence of carbonic acid gas, but with only low-to-moderate yields. Another unsatisfactory method, diacylation of biphenyl with acetyl chloride, as disclosed in U.S. Pat. No. 3,383,402, requires stoichiometric amounts of $AlCl_3$.

Methods also have been disclosed for the production of 4,4'-dicarboxybiphenyl from halogenated aromatic compounds. EP 0,206,543 teaches the coupling of p-chlorobenzoic acid, while U.S. Pat. No. 3,636,082 teaches carboxylation of 4,4'-dibromobiphenyl. Unfortunately, both methods have the potential to generate halogenated biphenyls as undesirable by-products.

U.S. Pat. No. 3,296,280 discloses the oxidation of 4-t-butyl-4'-carboxybiphenyl by $NO_2$ at high temperatures to produce 4,4'-dicarboxybiphenyl, but the examples show that the reaction proceeds only in low yield and produce undesirable nitrated by-products. Oxidation of 4,4'-dimethylbiphenyl by $NO_2$ has been reported in U.S. Pat. No. 3,631,097, but there is currently no economical route to 4,4'-dimethylbiphenyl. All economical syntheses of methyl-substituted biphenyl produce a mixture of isomers with a low yield of the p,p'-isomer.

A need remains for an improved process to oxidize t-alkyl aromatics to acids and to produce para-oriented aromatic acids.

SUMMARY OF THE INVENTION

It is an object of this invention to provide a process for oxidation of t-alkyl aromatics using molecular oxygen.

Another object of this invention is to provide a catalyst composition for efficient oxidation of t-alkyl aromatics.

It is yet another object of this invention to provide an improved process for the production of p,p'-dicarboxy aromatics.

It is a further object of the invention to provide process for the synthesis of p,p'-dicarboxypolyphenyl which uses low cost reactants and proceeds with good yield.

This invention contemplates a process for the production of aromatic acids which comprises oxidizing with oxygen at least one alkyl substituent attached to the aromatic ring through a tertiary carbon atom, in the presence of a catalytic amount of a catalyst composition comprising a cobalt salt, a minor amount of a manganese salt, and a halide selected from the group consisting of chlorides and fluorides, the oxidizing being carried out in a solvent for the reactants and intermediates, the solvent comprising an organic aliphatic carboxylic acid having from 2 to about 5 carbon atoms. Preferably, the solvent may also contain an aromatic co-solvent, and more preferably the solvent and/or the co-solvent is the halide. In one of its specific aspects, this invention contemplates a process for the production of p,p'-dicarboxypolyphenyl which comprises oxidizing p,p'-di-t-alkylpolyphenyl with molecular oxygen.

Another aspect of the invention contemplates an overall process for the production of para dicarboxy aromatics from aromatic starting materials (precursor aromatic compound) which comprises first preparing para-oriented di-alkyl aromatics by regioselective alkylation of the precursor aromatic compound with t-alkyl radicals and then oxidizing the para-oriented t-alkyl substituents of the alkyl-substituted aromatic compound with molecular oxygen in the presence of the catalyst of this invention.

It has been discovered that adding minor amounts of a manganese salt to a cobalt salt promotes the oxidation of tertiary-alkyl aromatics to carboxy aromatics in surprising good yield, using molecular oxygen as the oxidant. This discovery makes it possible to efficiently produce para-oriented dicarboxy aromatic acids desired by the art.

DETAILED DESCRIPTION OF THE INVENTION

In accordance with the method of this invention, carboxy aromatics are prepared by catalytic auto-oxidation of alkyl radicals attached to aromatic rings of an alkyl-substituted aromatic compound by a quaternary carbon. The oxygen can be supplied as air, as pure oxygen gas, or as oxygen diluted with other inert gases, for example nitrogen or carbon dioxide.

The reactant to be oxidized is an alkyl-substituted aromatic compound having one or more tertiary-alkyl substituents, such as tertiary-butyl or tertiary-amyl, attached to the aromatic ring thereof through the resulting quaternary carbon. The ring structure can be monocylic such as benzene, polyphenyls such as biphenyl, terphenyl, or polycyclic compounds, such as naphthalene or anthracene. The alkyl-substituted aromatic compounds suitable as reactants in this reaction also include alkyl-substituted diphenyl ethers. Reactants can also contain other substituents; however, alkyl substituents attached to the aromatic ring through primary or secondary carbons will also be converted to carboxy substituents during the oxidation. The alkyl-substituted aromatic compounds suitable as reactants can also contain other carboxy groups attached to the aromatic ring thereof, for example, 4-t-butyl-4'-carboxy biphenyl which would be converted to 4,4'-dicarboxy biphenyl.

A t-alkyl radical attached to an aromatic ring is normally resistant to oxidation, but this invention provides a novel catalyst composition which allows the oxidation to occur. The catalyst composition comprises one or more cobalt salts, a minor amount of one or more manganese salts and a source of a halide selected from chloride and fluoride, all of which are soluble in the reaction solvent. These components are present in a molar ratio of about 1:0.001–0.5:1–2 for Co:Mn:halide, for example, Co:Mn:Cl. In other words, about 0.001 to about 0.5 moles of manganese are present for each mole of cobalt present, and about 1 to about 2 moles of, for example, chloride are present for every mole of cobalt. These components are dissolved in a solvent that preferably is resistant to oxidation. Each of the metal salts and the chloride source may be added to the oxidation reaction separately, or they may be preblended in a solvent before addition to the reaction medium.

The cobalt can be supplied in the form of any cobalt salt which is soluble in the reaction medium. Examples include, but are not limited to, cobalt acetate, cobalt chloride, and cobalt sulfate. Generally, the cobalt salt is present in amounts of from about 0.0005 to about 0.20 moles, preferably about 0.001 to about 0.15 moles for each mole of aromatic reactant.

Manganese also can be supplied as any manganese salt that is soluble in the reaction medium. Examples include, but are not limited to manganese acetate and manganese chloride. Manganese should be present in a molar ratio to cobalt of about 0.001 to about 0.5, and preferably from about 0.025 to about 0.25. At levels of greater than or equal to about 1.0 moles per mole of cobalt, manganese inhibits the reaction.

The halide can be supplied as the salt of cobalt or manganese, but preferably it is supplied independently. Effective sources of the halide include, but are not limited to, halide salts that are soluble in the reaction medium at the reaction temperature, for example, sodium chloride, lithium chloride and the like and halo-alkyl and/or aryl compounds which are resistant to oxidation and, if solid, are soluble in the reaction medium at the reaction temperature or, if a liquid, are miscible in the reaction medium at the reaction temperature, for example, chlorobenzene. Other sources of chloride include hydrochloric acid, elemental chlorine, or an organic source such as chloroacetic acid, trichloroacetic acid, or butyl chloride. The use of bromide or iodide instead of chloride or fluoride, however, results in erratic behavior, low yields, and slow reaction, sometimes accompanied by explosion.

The catalyst level is a design choice that can easily be made by those skilled in the art. The amount of catalyst mixture, usually measured as a molar ratio between cobalt and the aromatic reactants, generally affects only the rate of the oxidation reaction.

A purpose of the solvent is to dissolve the catalyst, reactants and intermediates. The solvent comprises an organic aliphatic acid, having 2 to about 5 carbon atoms, and may be either a monocarboxylic or dicarboxylic acid. Acetic acid is particularly preferred. If desired, the solvent may further comprise an aromatic co-solvent to assist in dissolving the reactants. This is particularly important if the reactants contemplated are sparingly soluble or insoluble in a polar organic such as the aliphatic acid. The co-solvent can be any aromatic compound that is liquid at reaction temperatures and preferably is oxidation resistant. The oxidation resistant aromatic co-solvent is preferably selected from the group consisting of benzene, chlorobenzene, dichlorobenzene, trichlorobenzene, benzoic acid and biphenyl, more preferably, chlorobenzene, dichlorobenzene and trichlorobenzene, thereby being the halide source also, and most preferably, chlorobenzene. Preferably, both the aliphatic acid and the aromatic co-solvent are present.

The choice of solvent and the relative amounts or proportions of the aliphatic acid and the aromatic co-solvent, if any co-solvent is used, are adjusted as needed to ensure dissolution of the catalyst and reactants during the reaction. Thus, the ratio of these two components will depend on the catalyst, the reactants, and the reaction temperature in the particular reaction contemplated. Part of the reactant may be in suspension at the beginning of the reaction, so long as it dissolves during the course of the reaction. Determination of the appropriate proportions can easily be accomplished by one of ordinary skill in the art.

In general, the reaction will be conducted at a temperature between about 50° C. and about 300° C., preferably between about 75° C. and about 220° C., and most preferably between about 150° C. and about 175° C. In any case, the reaction temperature will depend in part on the melting points of the reactant and solvents.

The reaction is usually conducted at pressures of about 50 psig or greater, preferably between about 100 and about 500 psig. The reaction can be conducted at atmospheric pressure and moderate temperature, so long as the reactants are liquid, although the rate of reaction will be slower. Desirably, the reaction is run under conditions such that it is not mass transport limited with respect to oxygen.

As indicated above, the reaction rate is sensitive to the concentrations of the catalyst and the reactants as well as the reaction temperature and pressure. Reaction times of about 4-8 hours have been used, but one of ordinary skill can easily manipulate the rate-sensitive variables to achieve longer or shorter reaction times.

While the catalytic oxidation process of this invention can be used to oxidize alkyl groups in any aromatic system, it is especially useful for the oxidation of tertiary alkyl groups, which cannot be conveniently oxidized by systems previously available in the art. Thus, in Holz (1972), t-butyl toluene was oxidized to produce t-butyl benzoic acid with traditional cobalt bromide catalysts. Using the process of this invention, oxidation of t-butyl toluene will produce phthalic acid.

In particular, this invention can be used in the production of para-dicarboxy aromatics, which are of great interest to the high-performance plastics industry. The sterically bulky tertiary-alkyl groups are self-directing in alkylation of aromatic systems, resulting in high yields of para-oriented isomers, such as p,p'-di-t-alkyl-biphenyl and p,p''-di-t-alkyl-p-terphenyl and analogously 2,6-di-t-alkylnaphthalene. An overall process for the production of para-oriented dicarboxyaromatic acids comprises first alkylating a precursor aromatic compound with a tertiary-alkyl group and then oxidizing the alkyl-substituted aromatic compound with molecular oxygen in the presence of the catalyst of this invention.

The preferred precursor aromatic compounds to be alkylated in this reaction are benzene; polyphenyls, including biphenyl, terphenyl and quadraphenyl; fused polycylic compounds, such as naphthalene and anthracene; and aromatic ethers, such as diphenyl ether. The most preferred precursor aromatic compounds are biphenyl and p-terphenyl. Other aromatic reactants suitable for alkylation by this reaction will be apparent to those skilled in the art.

The t-alkyl radical for attachment to the precursor aromatic compound is supplied in the form of a substituted t-alkyl compound, such as t-alkylchloride, t-alkylbromide, t-alkanol, or t-alkyl methyl ether. The use of t-alkyl chloride or t-alkanol is preferred. A preferred radical is tertiary-butyl (t-butyl), and a preferred source of the t-butyl radical is isobutylene.

The alkylation of the precursor aromatic compound by a source of t-alkyl radical is catalyzed by any one of a variety of general acid catalysts including Bronsted acids and Lewis acids. In general, Friedel-Crafts-type Lewis acids, such as ferric chloride, aluminum chloride or stannic chloride, have been found to be more effective than strong Bronsted acids, such as trifluoroacetic acid or sulfuric acid.

The alkylation reaction is conveniently conducted at room temperature and atmospheric pressure, although those of ordinary skill in the art will recognize that higher temperatures can be used and that elevated reaction temperature will accelerate the reaction. When using temperatures at which the reactants are liquid, no solvent is necessary. When the reaction temperature is below the melting point of the mixture of reactants, the reactants should be dissolved in a solvent to achieve a homogeneous reaction mixture. The preferred solvents for the alkylation reaction are methylene chloride or chloroform, although other suitable solvents will be readily apparent to those of ordinary skill in the art. The conditions of reaction, including temperature, pressure and time, as well as the choice of solvent and the relative proportions of the reactants can be easily established by those skilled in the art.

The para-oriented dialkyl aromatics produced by this alkylation can then be oxidized with molecular oxygen in the presence of the catalyst composition of this invention to produce dicarboxyaromatics desired by the art.

Further specific examples of the practice of this invention are provided below. These examples are included for illustrative purposes only and are not intended to limit the scope of the invention.

EXAMPLES

Preparation of Alkyl-Substituted Aromatic Compounds

EXAMPLE 1

Preparation of 4,4''-di-tert-butyl-p-terphenyl

In this example, 4,4''-di-tert-butyl-p-terphenyl was prepared. A one liter round bottom flask was equipped with a stirrer, and a vent which was connected to an inverted funnel. The inverted funnel was placed in water to absorb any HCl formed in the reaction. The flask had 220 cc of chloroform placed in it along with 86.8 mM p-terphenyl, 360 mM t-butylchloride and 6.0 mM ferric chloride as catalyst. The mixture was heated until the reaction began. The reaction was stopped after two hours. The solution was placed in a separatory funnel and washed with water, dried with excess magnesium sulfate and the excess chloroform removed by evaporation. The crude product was recrystallized from hot acetone to yield 5.85 grams of 99% pure 4,4''-di-tert-butyl-p-terphenyl.

By a similar procedure, 4,4'-di-tert-butyl biphenyl was prepared using biphenyl and either t-butyl chloride or isobutylene. 4,4'-di-iso-propyl biphenyl may similarly be prepared using biphenyl and iso-propyl chloride. 4,4'-di-iso-propyl biphenyl is also commercially available.

Preparation of Para,Para'-Dicarboxyl Polyphenyl

EXAMPLE 2

Auto-oxidation of 4,4'-di-tert-butyl biphenyl was carried out in a 300 ml Hastelloy C stirred autoclave from Autoclave Engineers Inc. equipped with a teflon liner, cooling coil and heater for temperature control, back pressure regulator and a flow controller for feed gas control. The autoclave was charged with 0.56 mM cobaltous acetate, 0.037 mM manganese (II) acetate, 0.75 mM hydrochloric acid, 37.5 mM 4,4'-di-tert-butyl biphenyl, 40 cc acetic acid, 60 cc chlorobenzene and 500 psig oxygen with flow through of 500 sccm. The autoclave was heated to 170° C. and held for 4 hours. The autoclave was cooled rapidly and the product removed. Analysis indicated 65% conversion of the 4,4'-di-tert-butyl biphenyl. The selectivity to 4,4'-biphenyl dicarboxylic acid was 40% of the 4,4'-di-tert-butyl biphenyl. No chlorinated aromatic compounds were produced.

EXAMPLE 3

The autoclave of Example 2 was charged with 0.56 mM cobaltous acetate, 0.037 mM manganese (II) acetate, 0.75 mM hydrochloric acid, 37.5 mM 4,4'-di-tert-butyl biphenyl, 40 cc acetic acid, 60 cc chlorobenzene and 1000 psig air with flow through of 500 sccm. The autoclave was heated to 170° C. and held for 4 hours. The autoclave was cooled rapidly and the product removed. Analysis indicated 62% conversion of the 4,4'-di-tert-butyl biphenyl. The selectivity to 4,4'-biphenyl dicarboxylic acid was 25% of the 4,4'-di-tert-butyl biphenyl. No chlorinated aromatic compounds were produced.

EXAMPLE 4

The autoclave of Example 2 was charged with 0.56 mM cobaltous acetate, 0.037 mM manganese (II) acetate, 0.75 mM hydrochloric acid, 37.5 mM 4,4'-di-tert-butyl biphenyl, 40 cc acetic acid, 60 cc chlorobenzene and 250 psig air with flow through of 500 sccm. The autoclave was heated to 170° C. and held for 4 hours. The autoclave was cooled rapidly and the product removed. Analysis indicated 52% conversion of the 4,4'-di-tert-butyl biphenyl. The selectivity to 4,4'-biphenyl dicarboxylic acid was 15% of the 4,4'-di-tert-butyl biphenyl. No chlorinated aromatic compounds were produced.

EXAMPLE 5

The autoclave of Example 2 was charged with 0.56 mM cobaltous acetate, 0.037 mM manganese (II) acetate, 0.75 mM hydrochloric acid, 37.5 mM 4,4'-di-tert-butyl biphenyl, 40 cc acetic acid, 60 cc chlorobenzene and 300 psig oxygen with flow through of 50 sccm. The autoclave was heated to 170° C. and held for 4 hours. The autoclave was cooled rapidly and the product removed. Analysis indicated 55% conversion of the 4,4'-di-tert-butyl biphenyl. The selectivity to 4,4'-biphenyl dicarboxylic acid was 20% of the 4,4'-di-tert-butyl biphenyl. No chlorinated aromatic compounds were produced.

EXAMPLE 6

In this comparative example, no manganese (II) acetate was utilized. Furthermore, the halide concentration was below that required herein. In this example, the autoclave of Example 2 was charged with 0.375 mM cobaltous acetate, 0.105 mM hydrochloric acid, 37.5 mM 4,4'-di-tert-butyl biphenyl, 40 cc acetic acid, 60 cc chlorobenzene and 300 psig oxygen with flow through of 500 sccm. The autoclave was heated to 170° C. and held for 4 hours. The autoclave was cooled rapidly and the product removed. Analysis indicated 3% conversion of the 4,4'-di-tert-butyl biphenyl. The selectivity to 4,4'-biphenyl dicarboxylic acid was 0% of the 4,4'-di-tert-butyl biphenyl.

EXAMPLE 7

A glass reactor equipped with feed gas and temperature controls as reactor in Example 2, and an efficient stirrer and condenser was charged with 1.31 mM cobaltous acetate, 0.145 mM manganese (II) acetate, 2.4 mM hydrochloric acid, 3.0 grams 4,4'-di-tert-butyl biphenyl, 10 cc acetic acid, 20 cc chlorobenzene and 80 psig oxygen with flow through of 500 sccm. The reactor was heated to 160° C. and held for 20 hours. The reactor was cooled and the product removed. Analysis indicated 100% conversion of the 4,4'-di-tert-butyl biphenyl. The selectivity to 4,4'-biphenyl dicarboxylic acid was 59% of the 4,4'-di-tert-butyl biphenyl. No chlorinated aromatic compounds were produced.

EXAMPLE 8

The reactor of Example 7 charged with 0.112 mM cobaltous acetate, 0.008 mM manganese (II) acetate, 0.15 mM hydrochloric acid, 7.5 mM 4,4'-di-tert-butyl biphenyl, 8 cc acetic acid, 12 cc chlorobenzene and 50 psig oxygen with flow through of 500 sccm. The reactor was heated to 170° C. and held for 4 hours. The reactor was cooled and the product removed. Analysis indicated 60% conversion of the 4,4'-di-tert-butyl biphenyl. The selectivity to 4,4'-biphenyl dicarboxylic acid was 20% of the 4,4'-di-tert-butyl biphenyl. No chlorinated aromatic compounds were produced.

EXAMPLE 9

Acetic Acid As Sole Solvent

This example demonstrates the effects of using an organic aliphatic carboxylic acid without an aromatic co-solvent. The autoclave of Example 2 was charged with 0.27 mM cobaltous acetate, 0.042 mM manganese (II) acetate, 0.53 mM hydrochloric acid, 19 mM 4,4'-di-tert-butyl biphenyl, 50 cc acetic acid and 1000 psig air with flow through of 200 sccm. The autoclave was heated to 170° C. and held for 4 hours. The autoclave was cooled rapidly and the product removed. Analysis indicated 31% conversion of the 4,4'-di-tert-butyl biphenyl. The selectivity to 4,4'-biphenyl dicarboxylic acid was 12% of the 4,4'-di-tert-butyl biphenyl. No chlorinated aromatic compounds were produced.

EXAMPLE 10

Comparative Example-Chlorobenzene As Sole Solvent

This example demonstrates the effects of a reaction without an organic aliphatic carboxylic acid present. The autoclave of Example 2 was charged with 0.27 mM cobaltous acetate, 0.042 mM manganese (II) acetate, 0.53 mM hydrochloric acid, 19 mM 4,4'-di-tert-butyl biphenyl, 50 cc chlorobenzene and 1000 psig air with flow through of 200 sccm. The autoclave was heated to 170° C. and held for 4 hours. The autoclave was cooled rapidly and the product removed. Analysis indicated 0% conversion of the 4,4'-di-tert-butyl biphenyl.

EXAMPLE 11

Comparative Example: Excessive Manganese Salt

The reactor of Example 7 was charged with 0.116 mM cobaltous acetate, 0.116 mM manganese (II) acetate, 0.23 mM hydrochloric acid, 7.5 mM 4,4'-di-tert-butyl biphenyl, 40 cc acetic acid, 60 cc chlorobenzene and 80 psig oxygen with flow through of 500 sccm. The autoclave was heated to 170° C. and held for 4 hours. The autoclave was cooled rapidly and the product removed. Analysis indicated 12% conversion of the 4,4'-di-tert-butyl biphenyl. The selectivity to 4,4'-biphenyl dicarboxylic acid was 1% of the 4,4'-di-tert-butyl biphenyl. As is readily apparent, molar concentration of Mn:Co of greater than or equal to about 1:1 inhibits the oxidizing reaction.

EXAMPLE 12

Oxidation of 4,4''-di-tert-butyl-p-terphenyl

The autoclave of Example 2 was charged with 0.375 mM cobaltous acetate, 0.037 mM manganese (II) acetate, 0.75 mM hydrochloric acid, 37.5 mM 4,4''-di-tert-butyl-p-terphenyl, 40 cc acetic acid, 60 cc chlorobenzene and 300 psig oxygen with flow through of 500 sccm. The autoclave was heated to 170° C. and held for 4 hours. The autoclave was cooled rapidly and the product removed. Analysis indicated 85% conversion of the 4,4'-di-tert-butyl-p-terphenyl. The selectivity to 4,4''-p-terphenyl dicarboxylic acid was 15% of the 4,4''-di-tert-butyl-p-terphenyl. No chlorinated aromatic compounds were produced.

EXAMPLE 13

Chlorinated Aromatic Solvent As Halide

This example demonstrates the effects of utilizing a chlorinated aromatic solvent as the source of halide and without any other halide present. The reactor of example 7 was charged with 1.28 mM cobaltous acetate, 0.127 mM manganese (II) acetate, 11.27 mM 4,4'-di-tert-butyl biphenyl, 30 cc acetic acid, 20 cc chlorobenzene and 80 psig oxygen with a flow of 500 sccm. The reactor was heated to 160° C. and held for 8 hours. The reactor was cooled and the product removed. Analysis indicated 48% conversion of the 4,4'-di-tert-butyl biphenyl. The selectivity to 4,4'-biphenyl dicarboxylic acid was 18% of the 4,4'-di-tert-butyl biphenyl.

EXAMPLE 14

Comparative Example: Co-Solvent Used and No Halide

This example demonstrates the effects of utilizing non-chlorinated aromatic solvent without any other halide present. The reactor of example 7 was charged with 1.28 mM cobaltous acetate, 0.127 mM manganese (II) acetate, 11.27 mM 4,4'-di-tert-butyl biphenyl, 30 cc acetic acid, 20 cc benzene and 80 psig oxygen with a flow of 500 sccm. The reactor was heated to 160° C. and held for 12 hours. The reactor was cooled and the product removed. Analysis indicated 8% conversion of the 4,4'-di-tert-butyl biphenyl. The selectivity to 4,4'-biphenyl dicarboxylic acid was 0% of the 4,4'-di-tert-butyl biphenyl.

EXAMPLE 15

Comparative Example: No Co-Solvent Used and No Halide

This example demonstrates the effects of not utilizing a halide nor a co-solvent in the catalyst system. The reactor of example 7 was charged with 1.28 mM cobaltous acetate, 0.127 mM manganese (II) acetate, 11.27 mM 4,4'-di-tert-butyl biphenyl, 50 cc acetic acid and 80 psig oxygen with a flow of 500 sccm. The reactor was heated to 160° C. and held for 12 hours. The reactor was cooled and the product removed. Analysis indicated 0% conversion of the 4,4'-di-tert-butyl biphenyl.

EXAMPLE 16

Oxidation of 4,4'-di-iso-propyl biphenyl

The autoclave of Example 2 was charged with 0.420 mM cobaltous acetate, 0.042 mM manganese (II) acetate, 0.84 mM hydrochloric acid, 41.94 mM 4,4'-di-iso-propyl biphenyl, 40 cc acetic acid, 60 cc chlorobenzene and 1000 psig air with flow through of 500 sccm. The autoclave was heated to 170° C. and held for 4 hours. The autoclave was cooled rapidly and the product removed. Analysis indicated 100% conversion of the 4,4'-di-iso-propyl biphenyl. The selectivity to 4,4'-biphenyl dicarboxylic acid was 75% of the 4,4'-di-iso-propyl biphenyl. No chlorinated aromatic compounds were produced.

It will be apparent from the foregoing that many other variations and modifications may be made in the processes and the compositions hereinbefore described, by those having experience in this technology, without departing from the concept of the present invention. Accordingly, it should be clearly understood that the processes and compositions referred to herein in the foregoing description are illustrative only and are not intended to have any limitations on the scope of the invention.

We claim:

1. A process for the production of an aromatic acid or acids from tertiary-alkyl substituted aromatic compounds, said process comprising oxidizing with oxygen a tertiary-alkyl group of a tertiary-alkyl substituted aromatic compound in a solvent in the presence of a catalytic amount of a catalyst composition comprising a cobalt salt, a manganese salt, and a halide selected from the group consisting of chlorides and fluorides, said manganese salt being present in a molar ratio of manganese to cobalt of from about 0.001:1 to about 0.5:1 and said halide being present in a molar ratio of halide to cobalt of from about 1:1 to about 2:1, said solvent comprising an organic aliphatic carboxylic acid having from 2 to about 5 carbon atoms.

2. The process of claim 1, wherein the tertiary-alkyl substituted aromatic compound contains two tertiary-alkyl groups.

3. The process of claim 1, wherein the tertiary-alkyl substituted aromatic compound is selected from the group consisting of p,p'-di-alkyl-biphenyl and p,p''-di-alkyl-terphenyl.

4. The process of claim 1, wherein the solvent is an organic aliphatic carboxylic acid having from 2 to about 5 carbons.

5. The process of claim 1, wherein the solvent further comprises an aromatic co-solvent.

6. The process of claim 1, wherein said tertiary-alkyl substituted aromatic compound is a para-oriented di-tertiary-alkyl aromatic compound prepared by alkylating a precursor aromatic compound with tertiary-alkyl radicals.

7. The process of claim 5, wherein the halide is the aromatic co-solvent.

8. The process of claim 6, wherein the aromatic co-solvent is chlorobenzene.

9. The process of claim 1, wherein said tertiary-alkyl substituted aromatic compound is a p,p'-di-t-butyl polyphenyl prepared by reacting a polyphenyl compound with isobutylene.

* * * * *